US009125944B2

(12) United States Patent
Oh et al.

(10) Patent No.: US 9,125,944 B2
(45) Date of Patent: Sep. 8, 2015

(54) BAB-TYPE TRI-BLOCK COPOLYMER COMPRISING POLYLACTIC ACID (A) AND POLYETHYLENE GLYCOL (B), METHOD FOR PRODUCING SAME, AND DRUG DELIVERY SYSTEM USING SAME

(75) Inventors: Kyung Taek Oh, Seoul (KR); Jeong Min Yun, Seoul (KR)

(73) Assignee: CHUNG-ANG UNIVERSITY INDUSTRY-ACADEMY COOPERATION FOUNDATION, Seoul (KR)

( * ) Notice: Subject to any disclaimer, the term of this patent is extended or adjusted under 35 U.S.C. 154(b) by 0 days.

(21) Appl. No.: 14/343,862

(22) PCT Filed: Oct. 31, 2011

(86) PCT No.: PCT/KR2011/008174
§ 371 (c)(1),
(2), (4) Date: Mar. 10, 2014

(87) PCT Pub. No.: WO2013/047946
PCT Pub. Date: Apr. 4, 2013

(65) Prior Publication Data
US 2014/0205638 A1    Jul. 24, 2014

(30) Foreign Application Priority Data
Sep. 29, 2011    (KR) .................. 10-2011-0099190

(51) Int. Cl.
*A61K 47/34*    (2006.01)
*A61K 9/10*    (2006.01)
(Continued)

(52) U.S. Cl.
CPC .............. *A61K 47/34* (2013.01); *A61K 9/1075* (2013.01); *C08G 63/664* (2013.01); *C08G 65/08* (2013.01); *C08G 81/00* (2013.01)

(58) Field of Classification Search
CPC ... Y10S 977/773; Y10S 977/906; A61K 9/14; A61K 9/16; A61K 9/50; A61K 9/51; A61K 9/1075
See application file for complete search history.

(56) References Cited

U.S. PATENT DOCUMENTS 5,929,177 A    7/1999   Kataoka
6,117,949 A *  9/2000   Rathi et al. .................... 525/415
(Continued)

FOREIGN PATENT DOCUMENTS

EP    0844269 A1    5/1998
EP    1539109 B1    9/2010
(Continued)

OTHER PUBLICATIONS

S Zhang, J Qing, C Xiong, Y Peng. "Synthesis of End-Functionalized AB Copolymers. II. Synthesis and Characterization of Carboxyl-Terminated Poly(ethylene glycol)-Poly(amino acid) Block Copolymers." Journal of Polymer Science: Part A: Polymer Chemistry, vol. 42, 2004, pp. 3527-3536.*
(Continued)

*Primary Examiner* — Isaac Shomer
(74) *Attorney, Agent, or Firm* — Revolution IP, PLLC

(57) ABSTRACT

Provided are a BAB-type tri-block copolymer including a polylactic acid (A) that is a hydrophobic block and polyethylene glycol (B) that is a hydrophilic block, a method of preparing the BAB-type tri-block copolymer including synthesizing a polylactic acid (A)-polyethylene glycol (B) di-block copolymer by a ring opening polymerization of a lactic acid monomer using a hydroxyl group of polyethylene glycol (B) as a polymerization initiator; and synthesizing a BAB-type tri-block copolymer by reacting the AB-type di-block copolymer with polyethylene glycol (B) including at least one carboxyl group at one or more terminals thereof in the presence of a coupling agent and a catalyst, and a drug delivery system using the BAB-type tri-block copolymer.

11 Claims, 9 Drawing Sheets

(51) Int. Cl.
  *C08G 81/00* (2006.01)
  *C08G 65/08* (2006.01)
  *C08G 63/664* (2006.01)
  *A61K 9/107* (2006.01)

(56) References Cited

U.S. PATENT DOCUMENTS

| | | | |
|---|---|---|---|
| 6,322,805 B1 * | 11/2001 | Kim et al. | 424/426 |
| 6,616,941 B1 | 9/2003 | Seo et al. | |
| 7,744,919 B2 | 6/2010 | Cho et al. | |
| 2008/0152616 A1 | 6/2008 | Seo et al. | |

FOREIGN PATENT DOCUMENTS

| | | |
|---|---|---|
| KR | 10-0360827 B1 | 11/2002 |
| KR | 10-2004-0021760 A | 3/2004 |
| KR | 10-0492805 B1 | 6/2005 |

OTHER PUBLICATIONS

A-K C Schmidt, CBW STark. "TPAP-Catalyzed Direct Oxidation of Primary Alcohols to Carboxylic Acids through Stabilized Aldehyde Hydrates." Organic Letters, vol. 13 No. 16, 2011, pp. 4164-4167, available online Jul. 27, 2011.*

* cited by examiner

BAB-TYPE TRI-BLOCK COPOLYMER COMPRISING POLYLACTIC ACID (A) AND POLYETHYLENE GLYCOL (B), METHOD FOR PRODUCING SAME, AND DRUG DELIVERY SYSTEM USING SAME

CROSS REFERENCE TO PRIOR APPLICATIONS

This application is a National Stage Application of PCT International Patent Application No. PCT/KR2011/008174 filed on Oct. 31, 2011, under 35 U.S.C. §371, which claims priority to Korean Patent Application Nos. 10-2011-0099190 filed on Sep. 29, 2011, which are all hereby incorporated by reference in their entirety.

TECHNICAL FIELD

One or more embodiments of the present invention are directed to a B A B-type tri-block copolymer including a polylactic acid (A) and polyethylene glycol (B), wherein a functional group at a terminal of the polyethylene glycol is changed, a method of preparing the same, and a drug delivery system by using the B A B-type tri-block copolymer.

BACKGROUND ART

Amphiphilic block copolymers include a hydrophilic block and a hydrophobic block, and in an aqueous solution, the hydrophobic block forms a core and the hydrophilic block forms a shell, thereby forming micelles each having a core-shell structure and a tens to hundreds nanometer-size.

Conventional amphiphilic block copolymers for preparing polymer micelles are categorized into a polymer that does not include a functional group and a polymer that includes a plurality of functional groups. The polymer that does not include a functional group may not sufficiently interact with hydrophobic drugs, and also has limitations on the development and application of a drug delivery system, and the polymer that includes a plurality of functional groups dissolves in water, and thus, may insufficiently encapsulate drugs (Korean Patent Publication No. 2004-0021760).

As a method of synthesizing a B A B-type tri-block copolymer by using AB-type initial polymer, a method of preparing a BA-AB type block copolymer by using a crosslinker is generally known, and examples of the crosslinker are hexamethylene diisocyanate and adipoyl chloride.

A B A B-type block copolymer prepared by using hexamethylene diisocyanate as a crosslinker is synthesized by urethane binding of hydrophobic A block (Jeong et al., nature, 388, 860-862, 1997). When adipoyl chloride is used as a crosslinker, a hydrochloric acid is formed as a by-product, and due to the hydrochloric acid, the hydrophobic A block may easily decompose (Feng Li et al., Langmuir, 23, 2778-2783, 2007).

In particular, a crosslinker for use in the preparation of a BA-AB type copolymer is reported as being toxic in vivo, and during reaction, AB-type initial polymer may decompose. Also, even the formed BA-AB type copolymer may be difficult to have a functional group at both ends of a hydrophilic B group. Accordingly, the copolymer is used as a drug delivery system having only a drug delivery purpose.

In response, the inventors of the present application, unlike the production of a BA-AB-type copolymer using hexamethylene diisocyanate and adipoyl chloride as a crosslinker, combined an AB-type initial polymer and an equivalent or different molecular weight of polyethylene glycol (B) to produce a B A B-type tri-block copolymer without the use of a crosslinker. By doing so, existing problems stemming from the use of a crosslinker are overcome, a block is formed to easily control the molecular weight of a polymer, and a symmetric or asymmetric copolymer having a varying molecular weight can be synthesized. Also, due to the introduction of polyethylene glycol, stability of the amphipilic polymer increases, and since a functional group at the terminal of the polyethylene glycol is changed to introduce functionality, targeting is possible and poor-soluble drugs may be encapsulated by a hydrophobic block of micelles formed by self-assembling such copolymers, leading to use of an intelligent drug delivery system.

DETAILED DESCRIPTION OF THE INVENTION

Technical Problem

An embodiment of the present invention provides a B A B-type tri-block copolymer for the preparation of a drug delivery system, enabling effective drug delivery, and the treatment and the imaging at the same time, by introducing a target material that maximizes therapeutic effects or a diagnosis material for imaging by using a polylactic acid (A), as a hydrophobic block, to form a core in a body fluid or an aqueous solution, and changing a terminal group of polyethylene glycol (B), as a hydrophilic block, and a method of preparing the B A B-type tri-block copolymer.

Another embodiment of the present invention provides a drug delivery system with high efficiency by introducing a target material that maximizes therapeutic effects or a diagnosis material for imaging by using a polylactic acid (A), as a hydrophobic block, to form a core in a body fluid or an aqueous solution, and changing a terminal group of polyethylene glycol (B) as a hydrophilic block.

Technical Solution

An aspect of the present invention provides a B A B-type tri-block copolymer that includes a polylactic acid (A) that is a hydrophobic block and polyethylene glycol (B) that is a hydrophilic block, and is a compound represented by Formula 1 below:

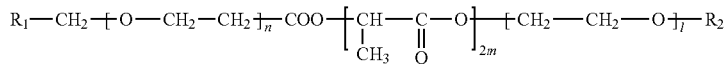

[Formula 1]

in Formula 1,
$R_1$ is H or $CH_2$—COOH,
$R_2$ is H, $CH_3$, or $CH_2$—$CH_2$—COOH,
m may be an integer of 7 to 70, and
l and n may each be an integer of 23 to 455.
In particular, the copolymer may be a compound represented by Formula 2 below:

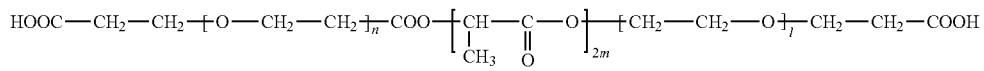

[Formula 2]

in Formula 2, m may be an integer of 7 to 70, and l and n may each be an integer of 23 to 455.

The polylactic acid (A) may be synthesized from a monomer selected from the group consisting of an L-lactic acid, a D-lactic acid, and an L,D-lactic acid, and may have a molecular weight of 2000 to 20000 daltons. In this regard, when the molecular weight of the polylactic acid (A) is outside this range, a lactic acid, which is an acidic final product, may be produced during decomposition in vivo, thereby causing adverse effects, or due to high hydrophobic properties, a drug may not be encapsulated well, and polymers may agglomerate to form tens or several micro-sized particles.

The polyethylene glycol (B) has at least one carboxylic group at one or more terminals thereof, and may have a molecular weight of 1000 to 20000 Daltons. In this regard, when the molecular weight of polyethylene glycol (B) is outside this range, a hydrophobic moiety is longer than a hydrophilic moiety, thereby causing a decrease in critical micelles concentration (CMC) and accordingly, forming larger micelles, and when the molecular weight is great, it is difficult to perform the synthesis.

The polyethylene glycol (B) may be a compound represented by Formula 3 below:

$$R_3 \underset{}{\overset{}{\text{---}}} \left[ O \underset{}{\overset{}{\text{---}}} \right]_n R_4 \quad \text{[Formula 3]}$$

in Formula 3, $R_3$ may be $CH_3$ or COOH, $R_4$ may be OH or COOH, and n may be an integer of 23 to 455.

The tri-block copolymer according to the present invention may include 5 to 95 wt % of the polylactic acid (A) and 5 to 95 wt % of polyethylene glycol (B), and a molecular weight of the copolymer may be in a range of 4000 to 60000 Daltons.

Another aspect of the present invention provides a method of preparing a B A B-type tri-block copolymer, wherein the method includes i) synthesizing a polylactic acid (A)-polyethylene glycol (B) di-block copolymer by ring opening polymerization of a lactic acid monomer by using a hydroxyl group of the polyethylene glycol (B) as a polymerization initiator; and ii) synthesizing a B A B-type tri-block copolymer by reacting the AB-type di-block copolymer and a polyethylene glycol (B) having at least one carboxyl group at one or more terminals in the presence of a coupling agent and a catalyst.

The B A B-type tri-block copolymer may be produced by stirring, heating, irradiating of ultrasonic wave, solvent evaporation using emulsion, forming of a matrix, or dialysis using an organic solvent, and these methods may be used alone or in combination. For example, the B A B-type tri-block copolymer may be produced in great quantities by using a bottom flask method using an organic solvent.

The coupling agent may be dicyclohexylcarbodiimide (DCC) and the catalyst may be dimethylaminopyridine (DMAP).

A molecular weight of the B A B-type tri-block copolymer according to the present invention may be easily controllable, thereby allowing production of copolymers having various molecular weights, and due to the introduction of polyethylene glycol, stability of the B A B-type tri-block copolymer increases. Also, since a functional group of at the terminal of polyethylene glycol is changed to introduce functionality, targeting is possible and poor-soluble drugs may be encapsulated by a hydrophobic block of micelles formed by self-assembling of such copolymers, leading to use of an intelligent drug delivery system.

Another aspect of the present invention provides a polymer micelles-type drug delivery system including the B A B-type tri-block copolymer and a bioactive substance that can be encapsulated by the B A B-type tri-block copolymer.

The drug delivery system may include 70 to 99.9 wt % of the B A B-type tri-block copolymer and 0.1 to 30 wt % of the bioactive substance that is encapsulated by the B A B-type tri-block copolymer.

A diameter of the polymer micelles is not particularly limited, and may be in a range of 10 nm to 500 nm, and the drug delivery system may be administered orally, transdermally, rectally, vaginally, subcutaneously, intravenously, intramuscularly, or intraperitoneally.

The bioactive material may be any of various materials that are used to treat, prevent or diagnose disease, and may include any one or at least two selected from the group consisting of a peptide or antibody-containing protein medicament, a hormone agent, an antimicrobial agent, an anticancer agent, a contrast medium, an antivirus agent, an antifungal agent, an anti hyperlipidemic agent, a steroidal agent, a non-steroidal anti-flammatory agent, an anti-depression agent, and an anti-hypertension agent.

Also, the polymer enables polymer micelles to effectively encapsulate a target material, an image tracer, or a gene chemically or physically. Accordingly, the copolymer may also be used as a tracer or gene carrier that can be used for target-orientation applications or molecular imaging.

BEST MODE

Figure 1:
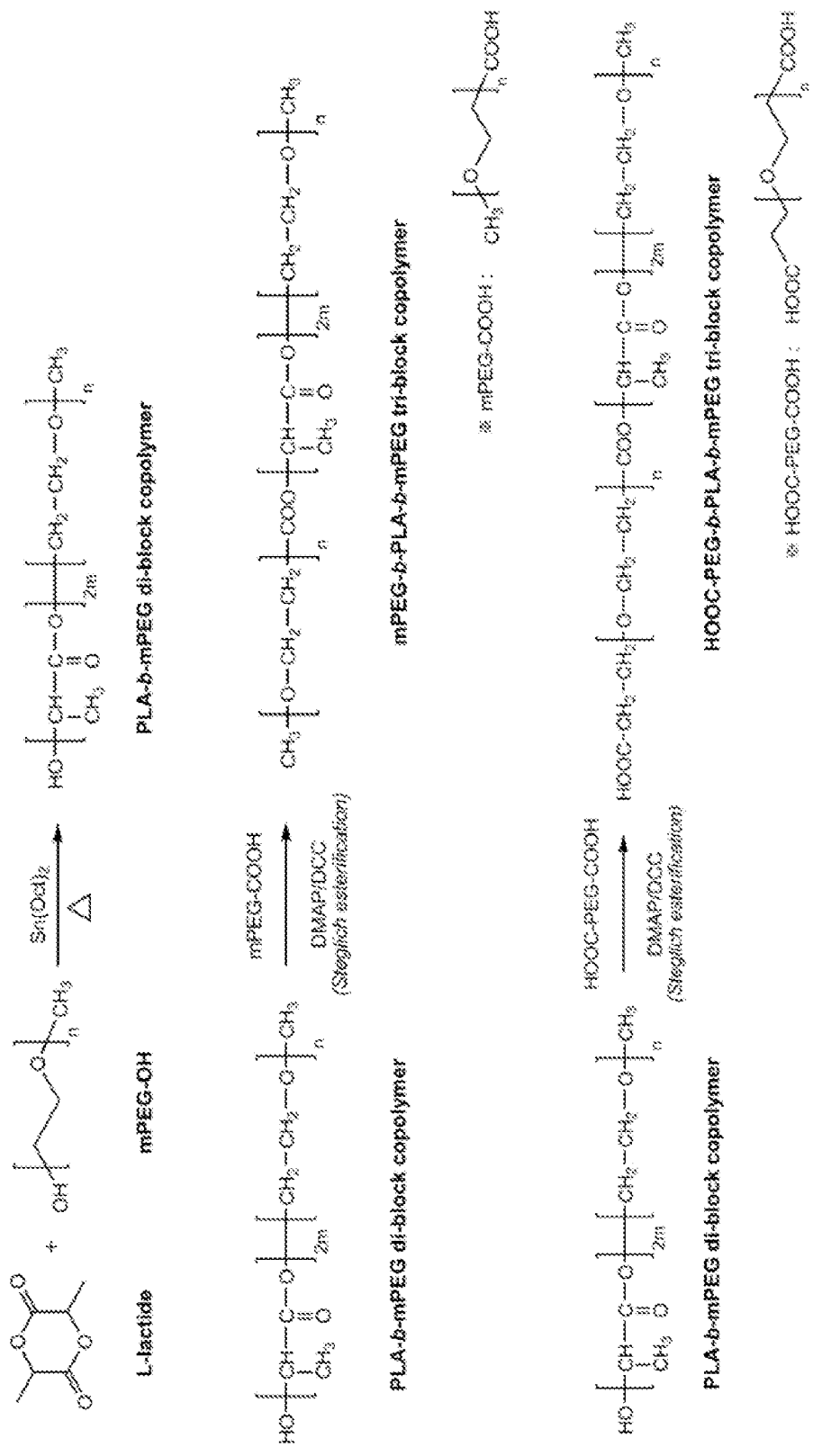
FIGS. 1 to 3 show reaction schemes for the preparation of a B A B-type tri-block copolymer according to embodiments of the present invention.

A B A B-type tri-block copolymer according to an embodiment of the present invention includes polylactic acid (A) that is a hydrophobic block and polyethylene glycol (B) that is a hydrophilic block, and is a compound represented by Formula 1 below:

$$R_1\text{---}CH_2\text{---}\left[O\text{---}CH_2\text{---}CH_2\right]_n\text{---}COO\text{---}\left[\underset{CH_3}{\overset{}{CH}}\text{---}\underset{O}{\overset{\parallel}{C}}\text{---}O\right]_{2m}\text{---}\left[CH_2\text{---}CH_2\text{---}O\right]_l\text{---}R_2 \quad \text{[Formula 1]}$$

in Formula 1,
$R_1$ is H or $CH_2$—COOH,
$R_2$ is H, $CH_3$, or $CH_2$—$CH_2$—COOH,
m may be an integer of 7 to 70, and
l and n may each be an integer of 23 to 455.

The copolymer may be a compound represented by Formula 2 below:

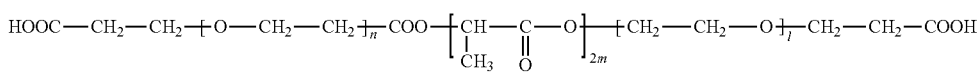

[Formula 2]

in Formula 2,
m may be an integer of 7 to 70, and
l and n may each be an integer of 23 to 455.

The polylactic acid (A) may be synthesized from a monomer selected from the group consisting of an L-lactic acid, a D-lactic acid, and an L,D-lactic acid.

A molecular weight of the polylactic acid (A) may be in a range of 2000 to 20000 daltons.

The polyethylene glycol (B) may include at least one carboxyl group at one or more terminals thereof.

A molecular weight of the polyethyleneglycol (B) may be in a range of 1000 to 20000 daltons.

The polyethylene glycol (B) may be a compound represented by Formula 3 below:

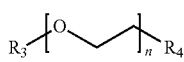

[Formula 3]

in Formula 3,
$R_3$ may be $CH_3$ or COOH,
$R_4$ may be OH or COOH, and
n may be an integer of 23 to 455.

The tri-block copolymer may include 5 to 95 wt % of the polylactic acid (A) and 5 to 95 wt % of the polyethylene glycol (B).

A molecular weight of the copolymer may be in a range of 4000 to 60000 Daltons.

A method of preparing a B A B-type tri-block copolymer according to an embodiment of the present invention includes i) synthesizing a polylactic acid (A)-polyethylene glycol (B) di-block copolymer by ring opening polymerization of a lactic acid monomer by using a hydroxyl group of the polyethylene glycol (B) as a polymerization initiator; and ii) synthesizing a B A B-type tri-block copolymer by reacting the AB-type di-block copolymer and a polyethylene glycol (B) having at least one carboxyl group at one or more terminals in the presence of a coupling agent and a catalyst.

A polymer micelles-type drug delivery system according to an embodiment of the present invention includes the B A B-type tri-block copolymer and a bioactive substance that can be encapsulated by the B A B-type tri-block copolymer.

The drug delivery system may include 70 to 99.9 wt % of a B A B-type tri-block copolymer and 0.1 to 30 wt % of a bioactive substance that is encapsulated by the B A B-type tri-block copolymer.

The bioactive material may include any one or at least two selected from the group consisting of a peptide or antibody-containing protein medicament, a hormone agent, an antimicrobial agent, an anticancer agent, a contrast medium, an antivirus agent, an antifungal agent, an anti hyperlipidemic agent, a steroidal agent, a non-steroidal anti-flammatory agent, an anti-depression agent, and an anti-hypertension agent.

The drug delivery system may be administered orally, transdermally, rectally, vaginally, subcutaneously, intravenously, intramuscularly, or intraperitoneally.

The polymer micelles may have a diameter of 10 to 500 Daltons.

MODE OF THE INVENTION

Embodiments of a method of preparing a B A B-type tri-block copolymer including a polylactic acid (A) that is a hydrophobic block and polyethylene glycol (B) that is a hydrophilic block will be described in detail. However, the embodiments do not limit the scope of the present invention.

Example 1

Synthesis of B A B-Type Tri-Block Copolymer

AB-type initial polymers having various molecular weights were synthesized, as disclosed in conventional literatures, by ring-opening polymerization of a lactic acid monomer by using a hydroxyl group (—OH) of polyethylene glycol as an initiator (S. K. Han et al., Colloids and Surfaces A: Physicohem. Eng. Aspects 214, 49-59, 2003). That is, 1 g of methoxy-PEG (mPEG-OH, MW 2000), 2 g of L-lactide, and stannous octoate (1 wt % of L-lactide), which is a catalyst, were dissolved in 50 ml of toluene at 60° C. in a round bottom flask equipped with a Dean-Stark trap. The polymerization of L-lactide initiated by hydroxyl group of methoxy-PEG was performed in nitrogen environment for 24 h at 120° C. The synthesized PLA-PEG was obtained by precipitation in diethyl ether (8-folds), subsequent filtration, and drying in vacuum for 2 days. In this regard, a molar ratio of polyethylene glycol to lactic acid monomer was changed to produce AB-type di-block copolymers having an average molecular weight of 1 kilo Daltons to 20 kilo Daltons.

To prepare a PEG-PLA-PEG tri-block copolymer, Steglich esterification was performed using the synthesized PLA-PEG and either monocarboxyl PEG (mPEG-COOH, MW 2000) or dicarboxyl PEG (dPEG-COOH, MW 2000). That is, PLA-PEG and either monocarboxyl PEG or dicarboxyl PEG were dissolved in dichloromethane (DCM) by stirring for 30 minutes. Dicyclohexylcarbodiimide (DCC, 1.25 molar ratio), which is a coupling agent, and dimethylaminopyridin (DMAP, 1 molar ratio), which is a catalyst, were added to the solution including the polymer. The reaction was carried out overnight and the final products were obtained by precipitation in diethyl ether (8-folds), subsequent filtration, and drying in vacuum for 2 days. This synthesis process is illustrated in detail in FIG. 1.

Example 2

Synthesis of B A B-Type Tri-Block Copolymer

Figure 2:
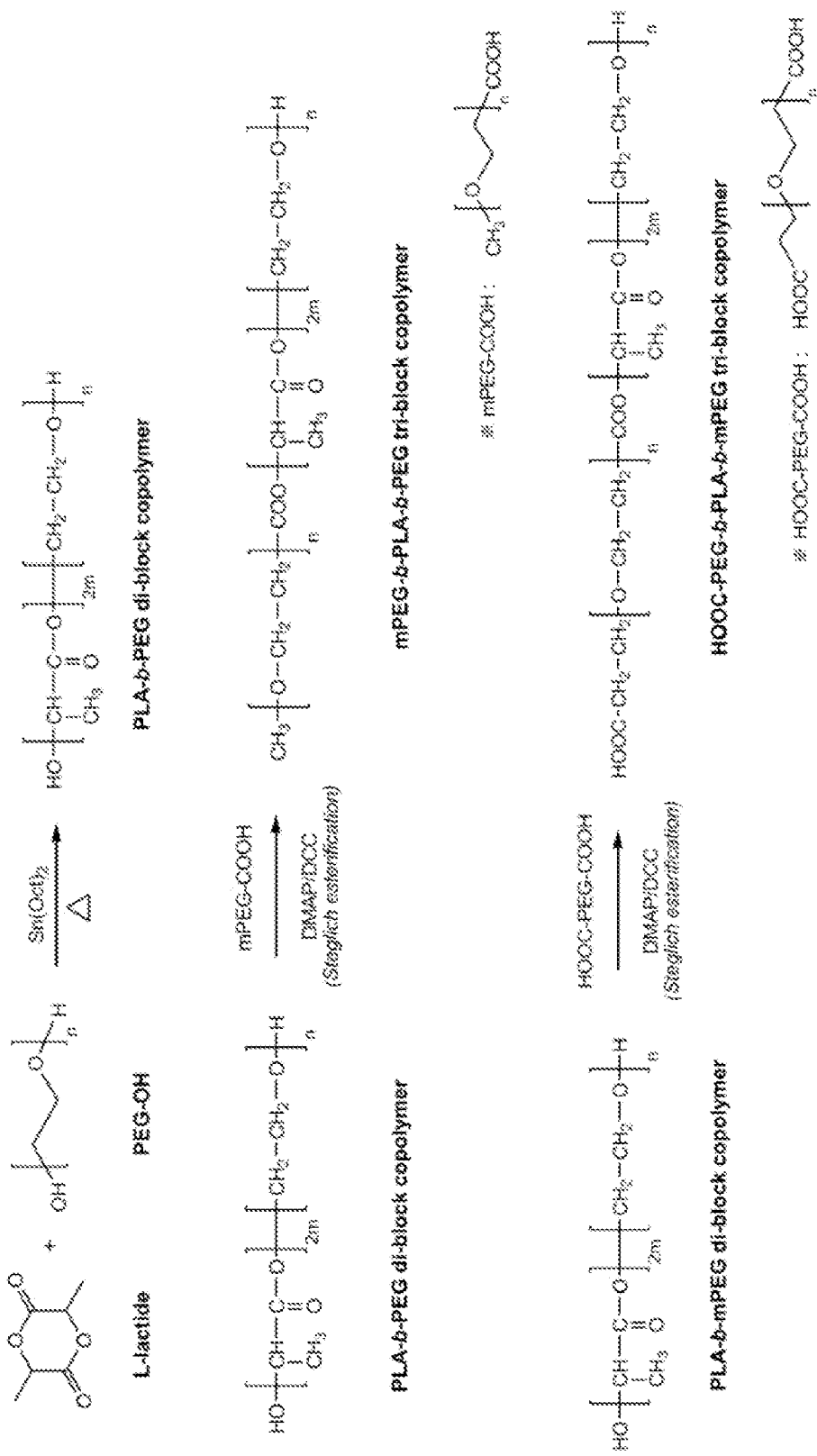

A B A B-type tri-block copolymer was synthesized in the same manner as in Example 1, except that PEG-OH (MW 2000) having a hydroxyl group at a terminal was used instead of methoxy-PEG (mPEG-OH, MW 2000). This synthesis process is illustrated in detail in FIG. 2.

Example 3

Synthesis of B A B-Type Tri-Block Copolymer

Figure 3:
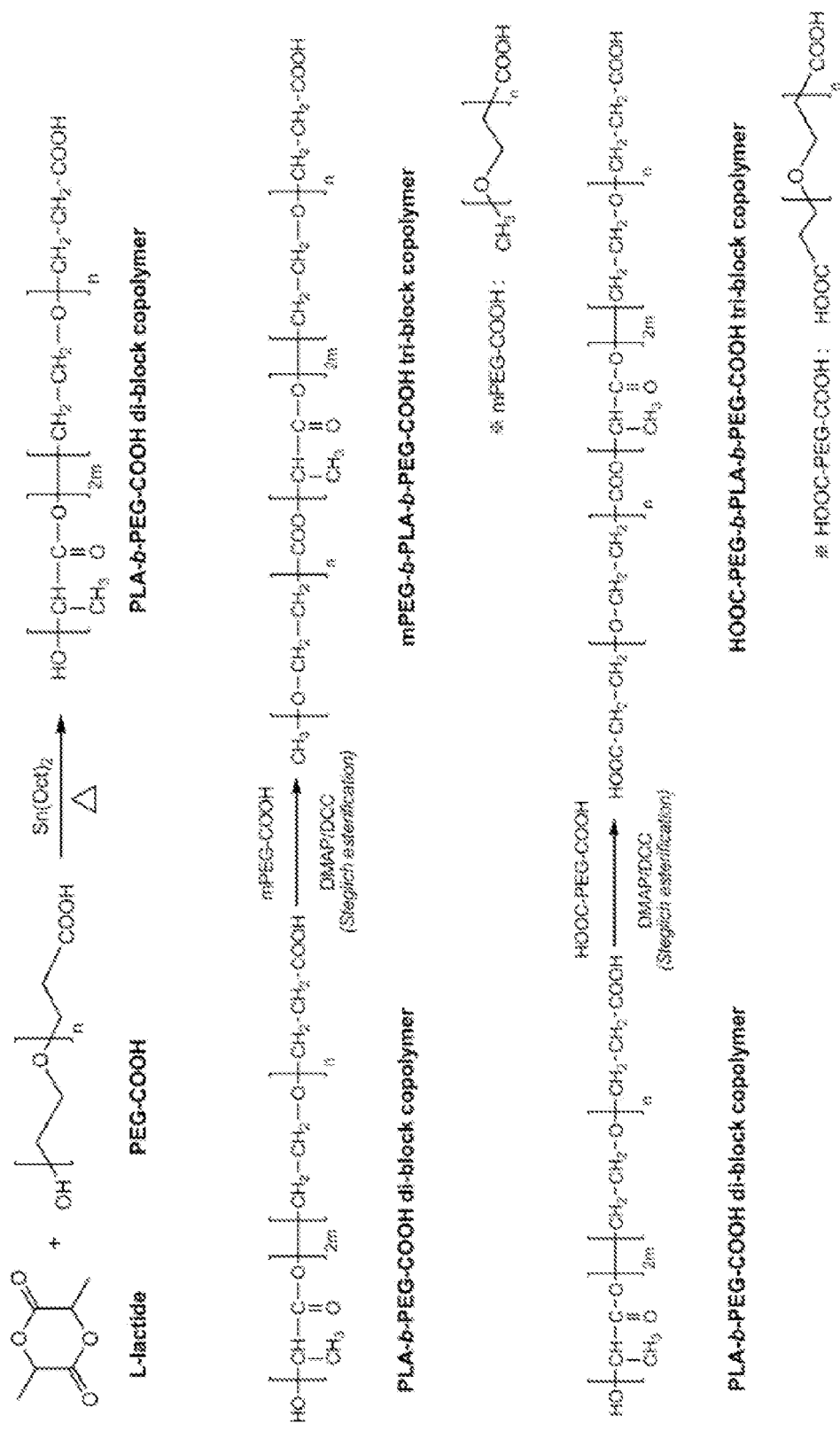

A B A B-type tri-block copolymer was synthesized in the same manner as in Example 1, except that PEG-OH (MW 2000) having a carboxyl group at a terminal was used instead of PEG-COOH (MW 2000). This synthesis process is illustrated in detail in FIG. 3.

Example 4

Analysis of Characteristics of B A B-Type Tri-Block Copolymer

Characteristics of the B A B-type tri-block copolymer prepared according to Example 1 were analyzed through $^1$H-NMR spectroscopy and gel permeation chromatography (GPC).

$^1$H-NMR spectroscopy was performed using Varian, Gemini 2000 (NMR 300 MHz) instrument, and CDCl$_3$ was used as solvent for analysis of copolymers. The molecular weight of the PLA segment was determined from $^1$H-NMR spectrum by examining the peak intensity ratio of the methane proton of the PLA segment (COCH(CH$_3$)O:$\delta$=5.2 ppm) and the methylene protons of the PEG segment (OCH$_2$CH$_2$: $\delta$=3.6 ppm) based on the molecular weight of PEG.

Figure 4:
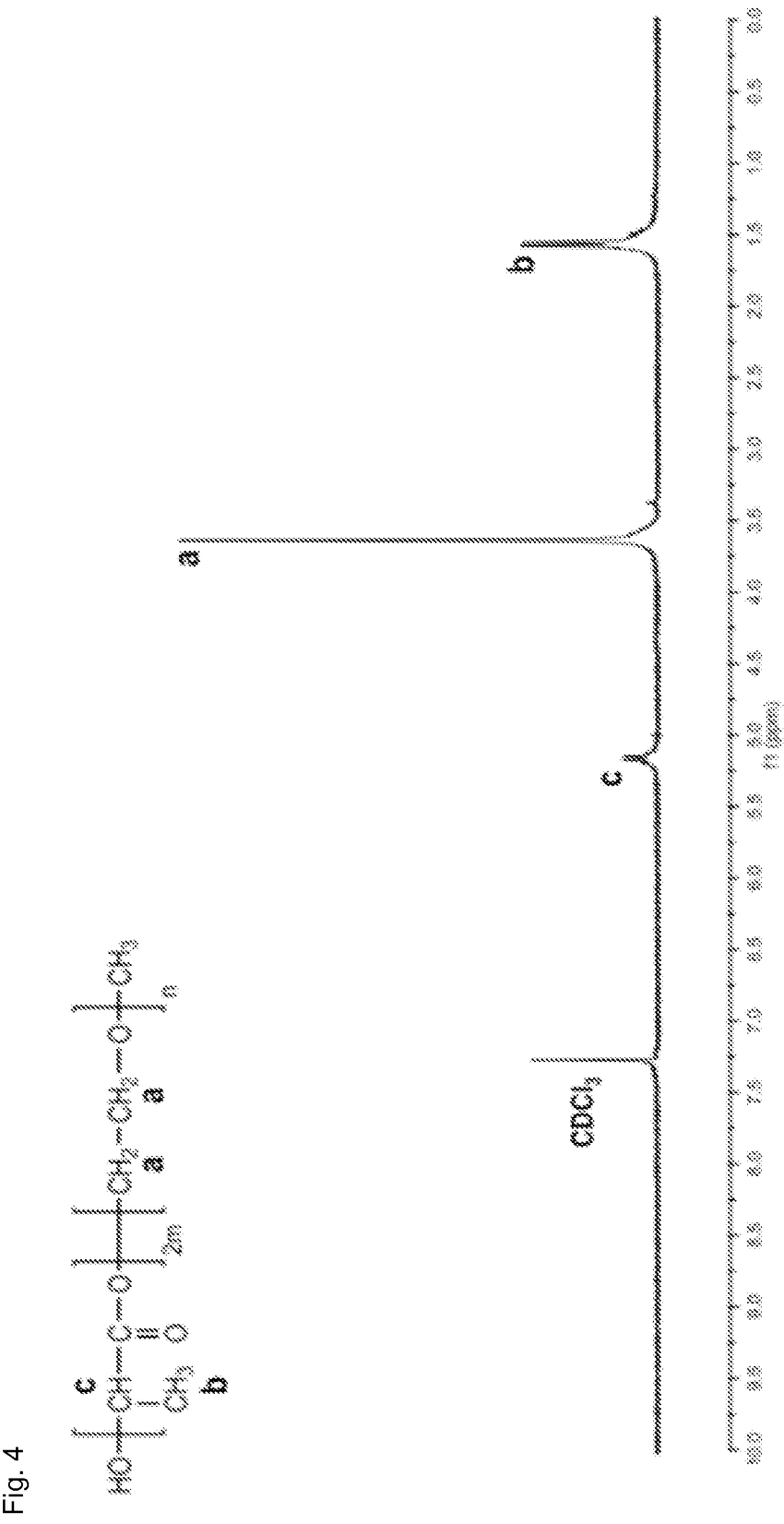
FIGS. 4 and 5 show $^1$H-NMR results of an AB-type copolymer and a B A B-type copolymer.

As a result, as illustrated in FIG. 4, the peaks of PLA protons appear at 1.5 ppm and 5.17 ppm, and the peak of PEG proton appears at 3.63 ppm, thereby confirming synthesis of the PLA-PEG di-block copolymer. The number average molecular weights (Mn) of synthesized PLA-PEG were 6032 and 5917 determined by $^1$H-NMR and GPC, respectively, and the yield was 73%. The polydispersity index (PDI) of the copolymer was 1.11 obtained from GPC, indicating the significantly narrow distribution of these polymers.

Figure 5:
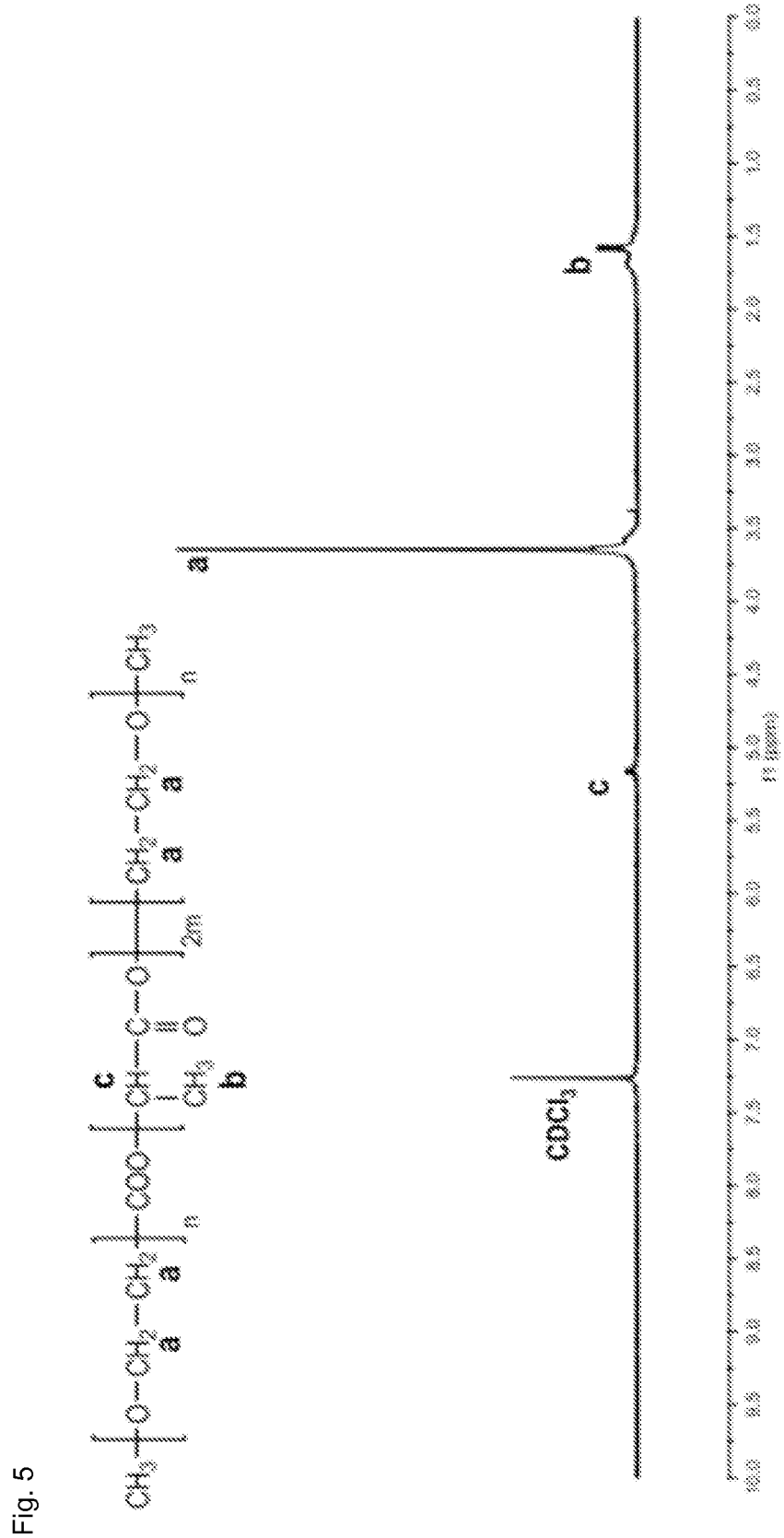

Also, as illustrated in FIG. 5, $^1$H-NMR results of the PEG-PLA-PEG showed the increase of PEG/PLA ratio proton peak compared to those of di-block copolymers. The number average molecular weights (Mn) of PEG-PLA-PEG were 7888 and 7510 determined by $^1$H-NMR and GCP, and the yield was 99% and PDI was 1.16.

In this regard, GPC was calculated by using polystyrene as a reference material, and $DP_{PLA}$ was calculated from the intensity ratio of methane proton of PLA segment and methylene proton of PEG segment.

TABLE 1

| Copolymer | $^1$H-NMR | | | | GCP | |
|---|---|---|---|---|---|---|
| | $DP_{PLA}$ | $Mn_{PLA}$ | $Mn_{PEG}$ | $Mn_{copolymer}$ | $Mn_{copolymer}$ | $Mw/Mn_{copolymer}$ |
| Di-block | 28 | 4032 | 2000 | 6032 | 5917 | 1.11 |
| Tri-block | 27 | 3888 | 4000 | 7888 | 7510 | 1.16 |

Example 5

Preparation of Self-Assembled Polymeric Micelles

AB-type and B A B-type copolymers prepared according to Example 1 were subjected to diafiltration method and bottom-flask method as described below to form micelles. In addition, the micelles were prepared by sonicating them in polystyrene tubes (FALCON®, Becton Dickinson, NJ) using a probe sonicator (Sonics VC505, Sonics & Materials, INC, CT) at 20% of 500 W for 1 min.

1. Diafiltration Method

PLA-PEG and PEG-PLA-PEG copolymers (10 mg) dissolved in 5 ml DMSO was transferred into a pre-swollen dialysis membrane tube, and dialyzed against a phosphate buffer saline (PBS, pH 7.4) solution. The outer aqueous phase was replaced with a fresh buffer solution several times for 24 hours.

2. Round Bottom-Blask Method 10 mg of each of PLA-PEG and PEG-PLA-PEG copolymers (10 mg) was dissolved in a volatile solvent, such as DCM or ACN. For the preparation of micelles, the organic phase was evaporated by rotary evaporation systems (EYELA n-1000, Tokyo, Japan), resulting in formation of a thin film in the round bottom flask. Rehydration of the film with PBS solution (pH 7.4) produces micelles.

Example 6

Micelles Characteristics Analysis

1. Size Distribution of Micelles Particles Evaluated Using Dynamic Light Scattering (DLS)

The change in size of the prepared micelles was measured using DLS. In detail, the effective hydrodynamic diameter ($D_{eff}$) of the particles was measured by photon correlation spectroscopy using a "Zetasizer Nano-ZS" (Malvern Instruments, UK) equipped with the Multi Angle Sizing Option (BI-MAS). At a scattering angle of 90°, the sizing measurements were performed in a thermostatic cell. Software provided by the manufacturer was used to calculate $D_{eff}$.

Figure 6:
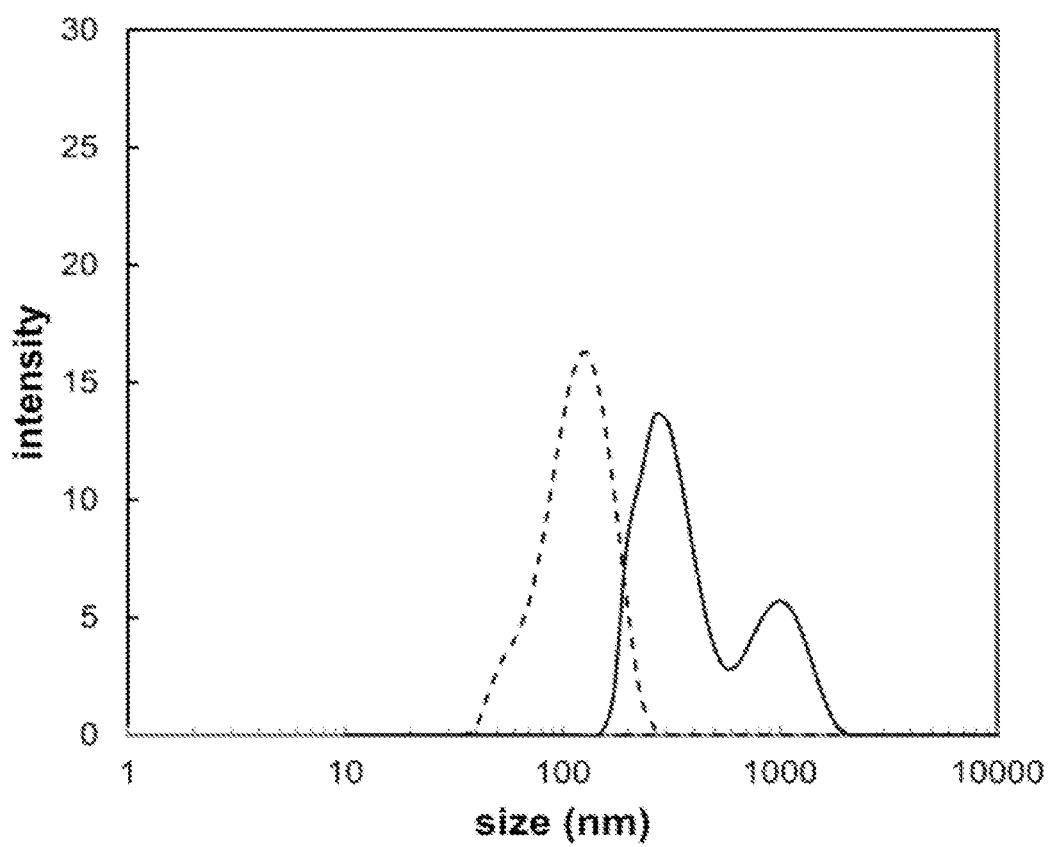
FIG. 6 is a size distribution diagram of micelles formed of an AB-type copolymer and a B A B-type copolymer.

As shown in FIG. 6, compared to the AB-type di-block copolymer, the B A B-type tri-block copolymer has a constant size and a narrow distribution.

Figure 7:
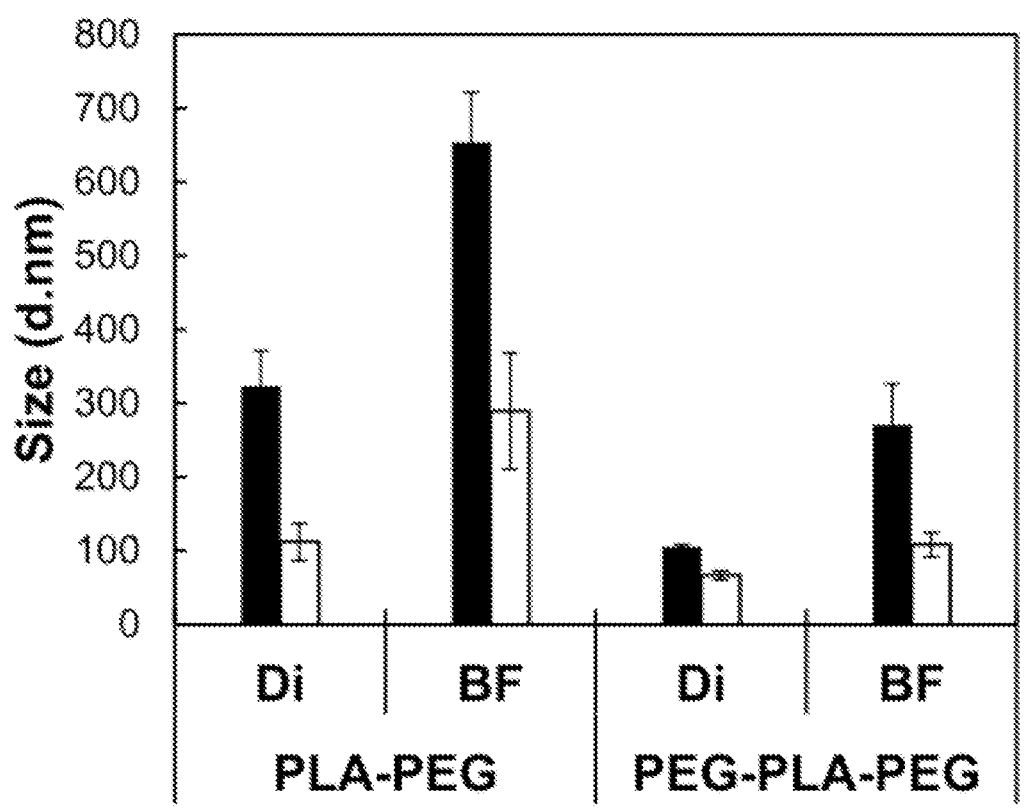
FIG. 7 shows graphs of diameters of micelles formed according to two different methods.

FIG. 7 shows difference of micelles prepared according to two different methods. That is, micelles prepared by diafiltration (Di) have smaller size than those prepared using a round-bottom flask method (BF), and in particular, in the case of B A B-type tri-block copolymer, the difference between when energy was provided (white bar) and when energy was not provided (black bar) is smaller than that of the AB-type polymer.

2. Critical Micelles Formation Concentration (CMC) Analysis

CMC of micelles was measured by using a fluorescence spectrometer (manufactured by Sinco) using pyrene, which is a hydrophobic luminescent material. Spectrofluorometer is equipped with polarizers for excitation (339 nm) and emission (374 nm). Pyrene was used as a fluorescent probe. Micelles with varying concentration were equilibrated with an aqueous pyrene solution ($6.0 \times 10^{-7}$ M) for 1 day under shielded light to load pyrene molecules into the micelle core. Excitation spectra of pyrene were recorded at $\lambda_{em}$ 372. The CMC was determined by plotting a ratio of $I_1$ (the intensity of the first peak) to $I_3$ (the intensity of the third peak) in an emission analysis profile with respect to $\log_{10}$ value of the micelles concentration. The CMC value was determined by the crossover point of low polymer concentrations on this plot.

Figure 8:
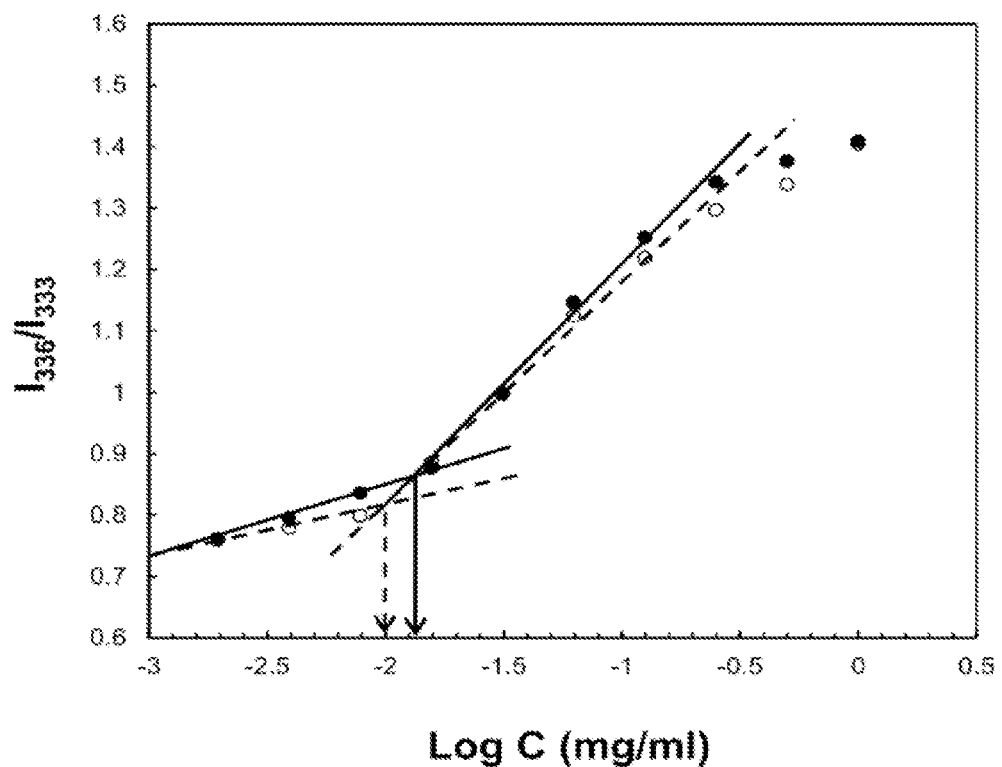
FIG. 8 is a graph of a ratio of $I_{336}$ to $I_{333}$ with respect to a micelles concentration when an excitation spectrum was detected at a wavelength of 372 nm.

The B A B-type tri-block copolymer, which has relatively low hydrophobicity of the polymer, had a higher CMC than the AB-type di-block copolymer. FIG. 8 shows a $I_{336}/I_{333}$ value at each concentration after excitation spectrum was detected at 372 nm.

3. Morphology of Micelles

The morphology of the polymeric micelles was examined using field emission scanning electron microscopy (FE-SEM, Hitachis-4800, Japan). Micelles samples were formed using a suspension of polymeric micelles dispersed in distilled water. A few drops of dilute dispersion were deposited onto a slide glass and dried in vacuum state. FE-SEM examinations were performed with platinum (Pt) coating on samples.

Figure 9:
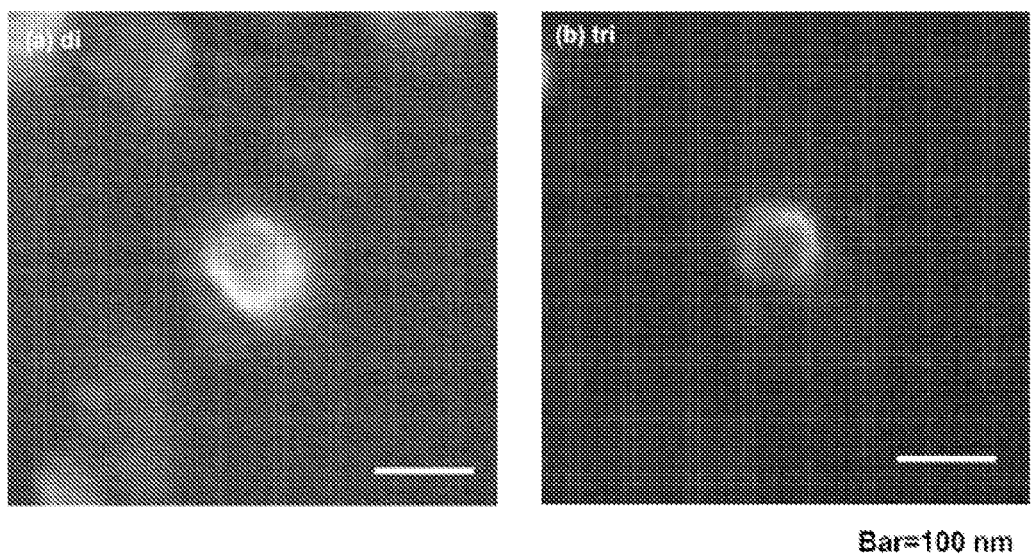
FIG. 9 shows scanning electron microscopic (SEM) images of an AB-type and B A B-type copolymers.

As a result, as illustrated in FIG. 9, it was confirmed that micelles were spherical and they showed results similar to those obtained from size distribution evaluated by DLS.

Example 7

Preparation of DOX-Loaded Micelles and In Vitro Drug Release Test

Doxorubicin hydrochloride (DOX.HCl) was stirred with 2 molar ratio of TEA in DMSO overnight of detach the HCl salt from DOX. 10 mg of polymer and 3 mg of DOX were dissolved in DMSO and DCM for diafiltration and bottom-flask method, respectively. The DOX-loaded micelles were prepared by the above methods. The concentration of DOX in micelles was determined by UV-VIS spectrometer (Genesys 10 UV) at λ=481 nm, and drug loading capacity and drug loading efficiency were calculated by using the following equations.

As shown in Table 2, in the case of encapsulation rates of DOX, the AB-type polymer showed 13.4±0.24 (Di) and 18.7±3.67 (BF) and the B A B-type copolymer showed 14.9±2.31 (Di) and 25.5±1.64 (BF).

Drug loading capacity (wt/wt %)=(amount of DOX loaded in micelles/initial loading amount of polymer and DOX)×100     <Equation 1>

Drug loading efficiency (%)=(amount of DOX loaded in micelles/initial loading amount of DOX)×100     <Equation 2>

TABLE 2

| Co-polymer | Preparation method | Loading capacity (%) | Loading efficiency (%) | Size (d · nm) |
|---|---|---|---|---|
| Di-block | Diafiltration | 13.4 ± 0.24 | 44.8 ± 0.79 | 259 ± 26.8 |
| | Round-bottom flask | 18.7 ± 3.67 | 62.5 ± 12.23 | 168 ± 38.2 |
| Tri-block | Diafiltration | 14.9 ± 2.31 | 49.7 ± 7.69 | 164 ± 10.5 |
| | Round-bottom flask | 25.5 ± 1.64 | 82.7 ± 9.61 | 186 ± 3.8 |

Figure 10:
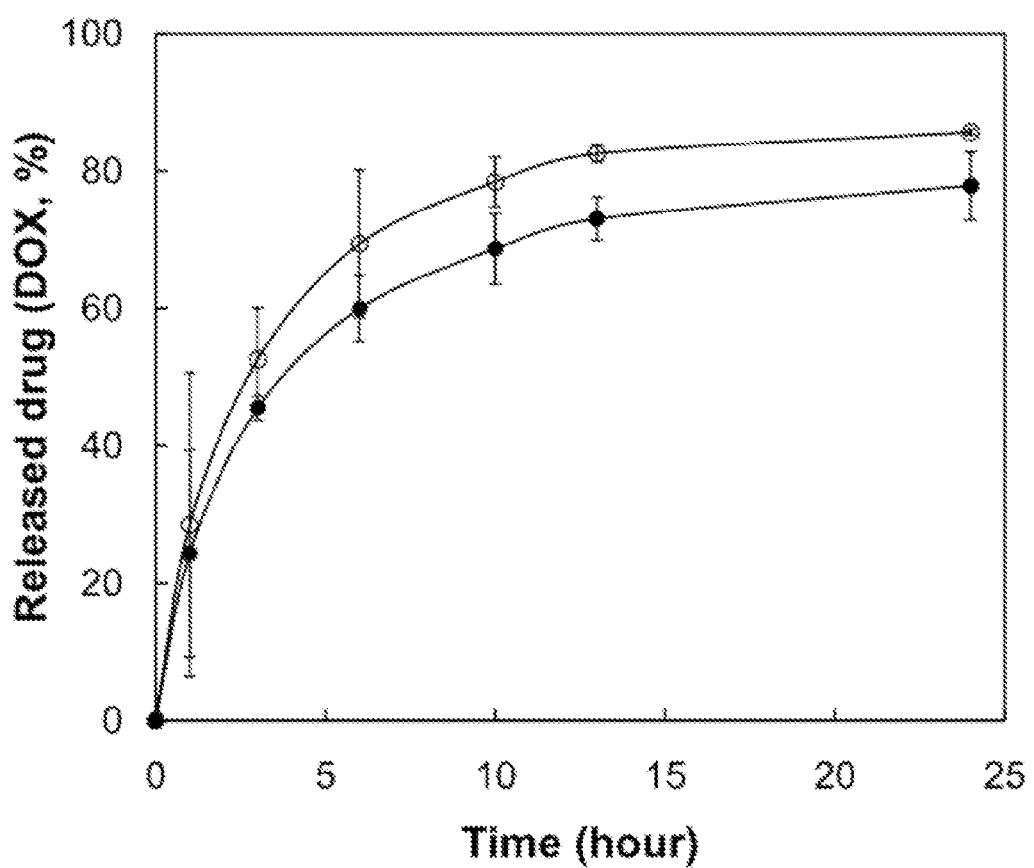
FIG. 10 shows drug release behaviors from drug loading micelles prepared with AB-type and B A B-type copolymers.

FIG. 10 shows evaluation results of drug release from DOX-loaded micelles prepared by using the round-bottom flask method with respect to time, and referring to FIG. 10, even when the amount of DOX released from the di-block copolymer is slightly greater than that of the tri-block copolymer, the two plots showed similar behaviors.

While the present invention has been particularly shown and described with reference to exemplary embodiments thereof, it will be understood by those of ordinary skill in the art that various changes in form and details may be made therein without departing from the spirit and scope of the present invention as defined by the following claims.

INDUSTRIAL APPLICABILITY

In general, poor-soluble drugs are used for the treatment after being encapsulated by a drug delivery system using a polymer to help absorption in vivo, such as micelles, liposome, emulsion, or micro/nano particles, and in the case of a drug delivery system having only the drug delivery purpose, many adverse effects occur according to a drug concentration. However, a micelles drug delivery system formed by self-assembling a B A B-type tri-block copolymer according to embodiments of the present invention enables targeting into a target area, such as tumors, inflammation, or brain, and even with a low drug concentration, high anti-cancer and anti-inflammation treatment effects may be obtained. Even with respect to particular disease other than cancer cells, the drug delivery system shows excellent drug delivery efficacy.

The invention claimed is:

1. A method of preparing a tri-block copolymer represented by the formula

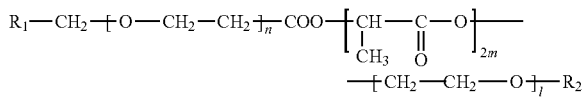

comprising the steps of:
(a) synthesizing a polylactic acid (PLA)-polyethylene glycol (PEG) diblock copolymer by a ring opening of a lactic acid monomer using methoxy-PEG-OH or hydroxyl-PEG-OH as an initiator; and
(b) esterification of the product of step (a) with dicarboxyl PEG in the presence of a coupling agent and a catalyst;

wherein,
$R_1$ is $CH_2$—COOH,
$R_2$ is H, or $CH_3$
m is an integer of 7 to 70, and
l and n are each integers of between 23 and 455.

2. The method of claim 1, wherein the polylactic acid is synthesized from a monomer selected from the group consisting of an L-lactic acid, a D-lactic acid, and an L,D-lactic acid.

3. The method of claim 1, wherein the polylactic acid has a molecular weight of 2000 to 20000 Daltons.

4. The method of claim 1, wherein the copolymer comprises 5 to 95 wt % of polylactic acid and 5 to 95 wt % of polyethylene glycol.

5. The method of claim 1, wherein the tri-block copolymer has a molecular weight of 4000 to 60000 Daltons.

6. A method of forming a polymer micelle drug delivery system comprising the steps of:
(a) producing a tri-block copolymer using the method of claim 1;
(b) forming said tri-block copolymer into a micelle encapsulating a bioactive agent.

7. The method of claim 6, wherein the drug delivery system comprises 70 to 99.9 wt % of the tri-block copolymer and 0.1 to 30 wt % of the bioactive substance being encapsulated by the tri-block copolymer.

8. The method of claim 6, wherein the bioactive material is selected from the group consisting of a peptide or antibody-containing protein medicament, a hormone agent, an antimicrobial agent, an anticancer agent, a contrast medium, an antivirus agent, an antifungal agent, an anti hyperlipidemic agent, a steroidal agent, a non-steroidal anti-inflammatory agent, an anti-depression agent, and an anti-hypertension agent.

9. The method of claim 6, further comprising the step of administering the drug delivery system orally, transdermally, rectally, vaginally, subcutaneously, intravenously, intramuscularly, or intraperitoneally.

10. The method of claim 6, wherein the polymer micelle diameter is in a range of 10 to 500 nm.

11. The method of claim 1,
wherein the coupling agent is dicyclohexylcarbodiimide (DCC); and
wherein the catalyst is dimethylaminopyridine (DMAP).

\* \* \* \* \*